(12) United States Patent
Stevens (10) Patent No.: US 10,028,860 B2
(45) Date of Patent: Jul. 24, 2018

(54) INTRAOCULAR IMPLANT

(76) Inventor: Julian Douglas Stevens, London (GB)

(*) Notice: Subject to any disclaimer, the term of this patent is extended or adjusted under 35 U.S.C. 154(b) by 490 days.

(21) Appl. No.: 13/492,653

(22) Filed: Jun. 8, 2012

(65) Prior Publication Data

US 2013/0331938 A1 Dec. 12, 2013

(51) Int. Cl.
- *A61F 9/00* (2006.01)
- *A61F 2/14* (2006.01)
- *A61F 2/16* (2006.01)
- *A61F 9/007* (2006.01)

(52) U.S. Cl.
CPC .............. *A61F 9/0017* (2013.01); *A61F 2/14* (2013.01); *A61F 2/16* (2013.01); *A61F 2/1632* (2013.01); *A61F 9/007* (2013.01); *A61F 2002/1681* (2013.01); *A61F 2220/0008* (2013.01)

(58) Field of Classification Search
CPC .................................. A61F 2/16; A61F 2/1632
USPC ... 623/5.11, 5.14, 5.15, 6.38–6.4, 6.44, 6.47, 623/6.49, 6.5
See application file for complete search history.

(56) References Cited

U.S. PATENT DOCUMENTS

| | | | |
|---|---|---|---|
| 4,124,905 A | 11/1978 | Clark | |
| 4,172,297 A * | 10/1979 | Schlegel | A61F 2/16 623/6.17 |
| 4,342,123 A * | 8/1982 | Gimbel | A61F 2/16 623/6.44 |
| 5,171,320 A * | 12/1992 | Nishi | A61F 2/16 623/6.39 |
| 5,366,499 A * | 11/1994 | Py | 623/5.15 |
| 5,476,512 A | 12/1995 | Sarfarazi | |
| 5,697,973 A | 12/1997 | Peyman | |
| 6,358,279 B1 * | 3/2002 | Tahi et al. | 623/4.1 |
| 2004/0098122 A1 * | 5/2004 | Lee | A61F 9/007 623/4.1 |
| 2006/0047339 A1 | 3/2006 | Brown | |

FOREIGN PATENT DOCUMENTS

WO WO 2007/082342 7/2007

OTHER PUBLICATIONS

European Application No. 10251496.5-2320, European Search Report dated Jan. 26, 2011, 8 pages.

* cited by examiner

*Primary Examiner* — Darwin Erezo
*Assistant Examiner* — Joshua Levine
(74) *Attorney, Agent, or Firm* — Patterson Thuente Pedersen, P.A.

(57) ABSTRACT

An intraocular implant for placement in the eye, e.g. as part of a cataract operation or crystalline lens extraction refractive operation, has at a peripheral portion of the implant a groove which engages with the lip of a single capsulotomy only formed in the lens capsule of the eye. The implant will normally be a lens, but may instead be a bung or plug for occluding an opening made in the capsule. The groove may be a continuous groove around the periphery of the implant, or there may be a series of individual spaced-apart grooves formed as projections protruding from the periphery. Instead of a single groove, a pair of axially spaced-apart grooves may be provided, which engage with respective capsulotomies formed in an anterior and a posterior part of the capsule. The posterior groove is preferably of a smaller mean diameter than the anterior groove.

16 Claims, 10 Drawing Sheets

PRIOR ART

Fig. 1

PRIOR ART

Fig. 2

PRIOR ART

Fig. 3

PRIOR ART

Fig. 4

PRIOR ART

Fig. 5

PRIOR ART

Fig. 6

PRIOR ART

PRIOR ART

Fig. 7(c)

PRIOR ART

# INTRAOCULAR IMPLANT

FIELD OF THE INVENTION

The invention relates to an intraocular implant, and in particular to an intraocular implant for use in cataract operations or refractive crystalline lens extraction operations generally.

BACKGROUND OF THE INVENTION

Figure 1:
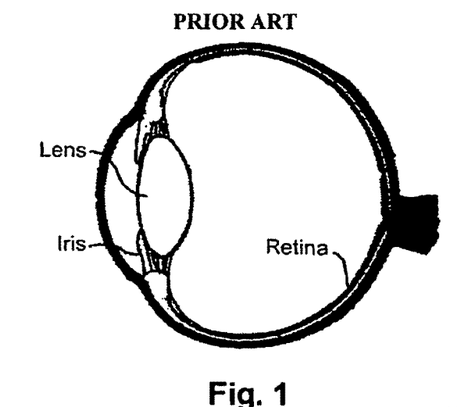
FIG. 1 is a sectional view of the human eye.

The cataract condition is a well known eye ailment, which these days, is easily treatable through surgery. The condition involves an opacification, yellowing or clouding of the natural crystalline lens (see FIG. 1), which is situated just behind the iris and serves to focus the incoming image onto the retina at the back of the eye.

The surgical procedure involves the removal of the opaque natural lens and its substitution by an artificial lens having the required focusing effect.

Figure 2:
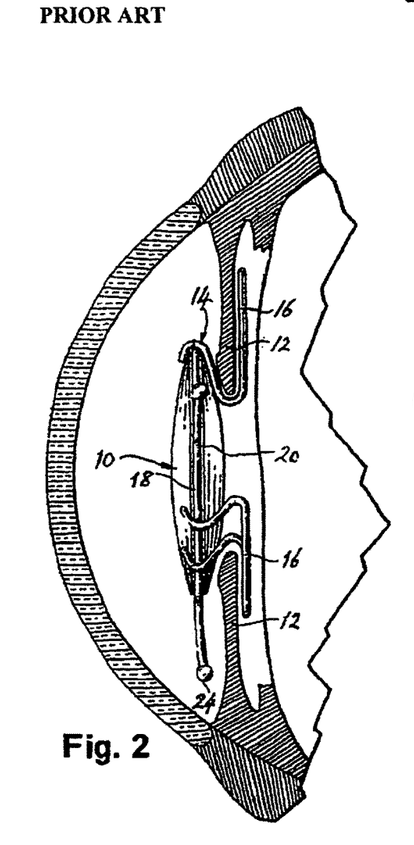
FIG. 2 is a part-side and part-sectional view of a human eye with an artificial lens substituted for the original lens in accordance with a known method.
Figure 3:
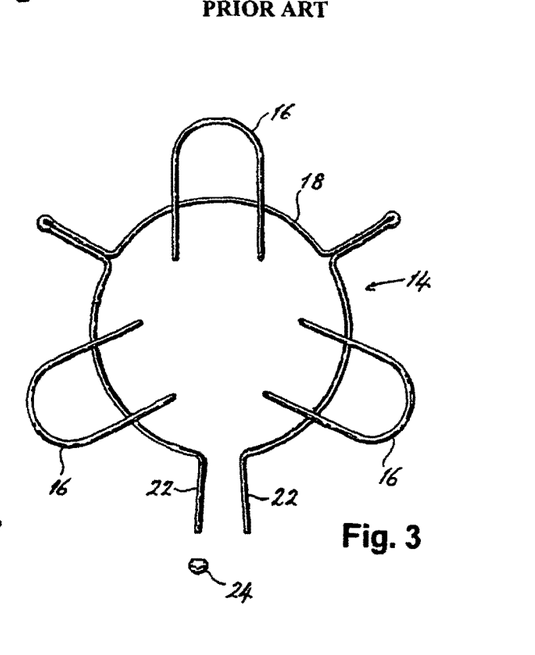
FIG. 3 depicts a haptic arrangement used in the known method of FIG. 2.

One way of achieving this is described in U.S. Pat. No. 3,925,825. FIGS. 2 and 3 correspond to FIGS. 1 and 2 of this patent, and show the placing of a lens 10 anterior to the iris 12. The lens is held in place against the iris by a haptic section 14. The haptic section 14 consists of a series of bent wire loops 16, which are attached to a circular wire frame 18. The lens 10 has a flat circumferential face 20 and the lens is held within the frame 18 by inserting the lens inside the frame 18 and closing the legs 22 of the frame so that the frame 18 closes tightly against the lens face 20. Once the legs 22 have been brought together, their ends are kept together via a terminal part 24.

Figure 4:
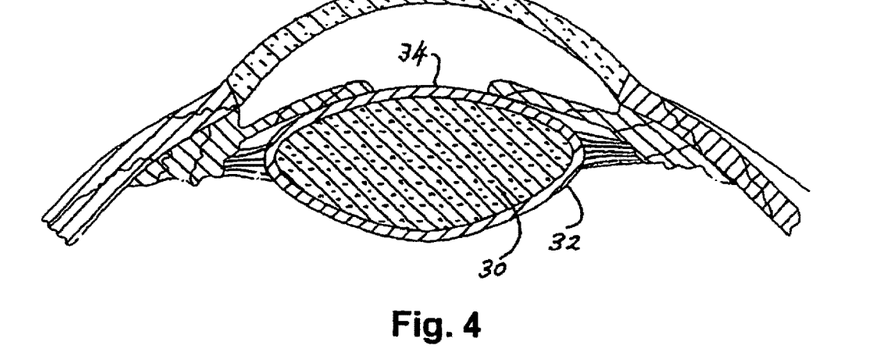
FIG. 4 is a sectional view of a human eye showing the natural lens in its capsule.

One way of extracting the opaque natural lens—a process known as extra-capsular extraction—will now be described. Reference is first made to US 2003/0130732, FIG. 1 of which corresponds to FIG. 4 of the present application. The lens 30 is accommodated within a so-called capsule, which is shown as item 32 in FIG. 4. To remove the opaque lens, an opening (a so-called "capsulotomy") is made in the anterior part 34 of the capsule 32 manually by a surgeon or by a pulsed laser and the lens 30 is removed through the opening.

To facilitate the removal of the opaque lens, the lens is first emulsified by the phacoemulsification method or by a pulsed laser. Phacoemulsification involves making a small incision in the cornea and introducing a very thin needle through the incision, which is then brought into contact with the lens through the capsulotomy. The needle is caused to vibrate at an ultrasonic frequency by the use of a magnetostrictive driver. The ultrasonic vibrations of the needle soften the lens and emulsify it. The emulsified parts can then be aspirated out of the capsule through the incision. Finally, the incision is widened sufficiently to introduce the substitute artificial lens into the capsule.

A pulsed laser can be used to create an opening in the capsule, by photoablating capsular tissue along a boundary having a predetermined profile, e.g., circular, oval or elliptical.

Figure 5:
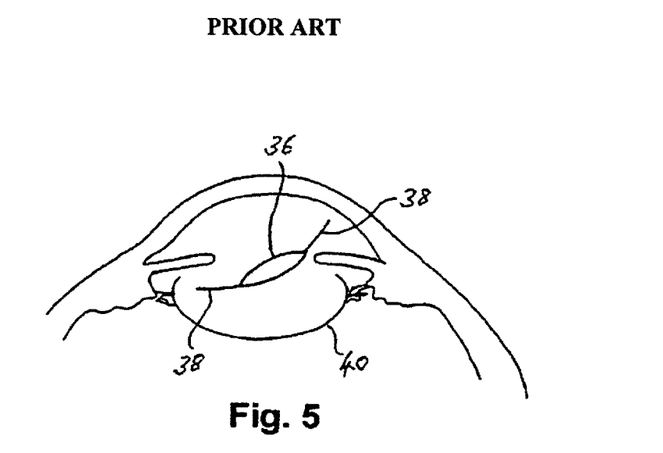
FIGS. 5 and 6 are sectional views showing two stages in a known lens replacement method employing extra-capsular extraction.
Figure 6:
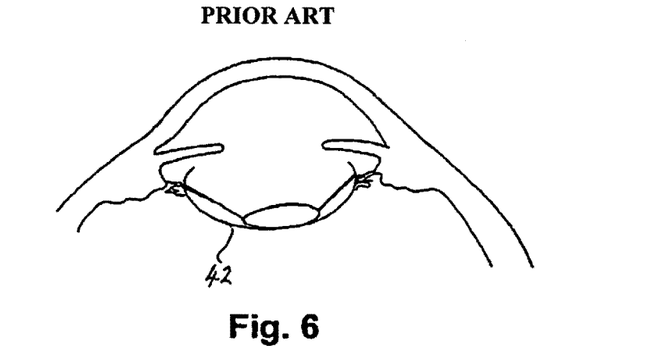

Like the lens of FIG. 2, the lens in the extra-capsular method is conventionally held within the capsule by the use of haptics. One example of this is shown in U.S. Pat. No. 5,376,115. FIGS. 5 and 6 are an extract from this patent, in which the artificial lens 36 with its haptics 38 is introduced through the iris and into the capsule 40 via the capsulotomy (FIG. 5) and finally brought to bear against the inside posterior surface of the capsule (FIG. 6). The haptics 38 are used to center the lens and secure it in place inside the capsule.

Figure 7A:
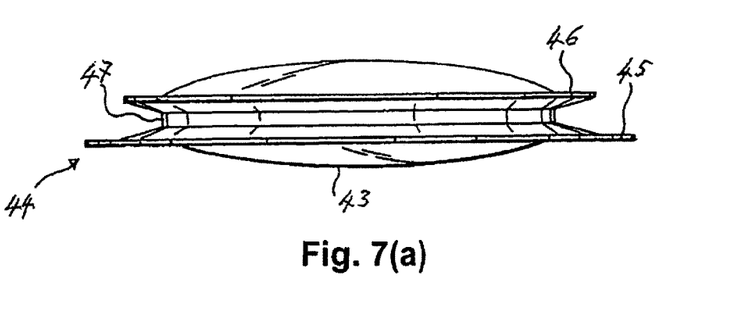
FIGS. 7(a)-7(c) are orthogonal views of a known "bag-in-lens" implant.
Figures 7B, 7C:
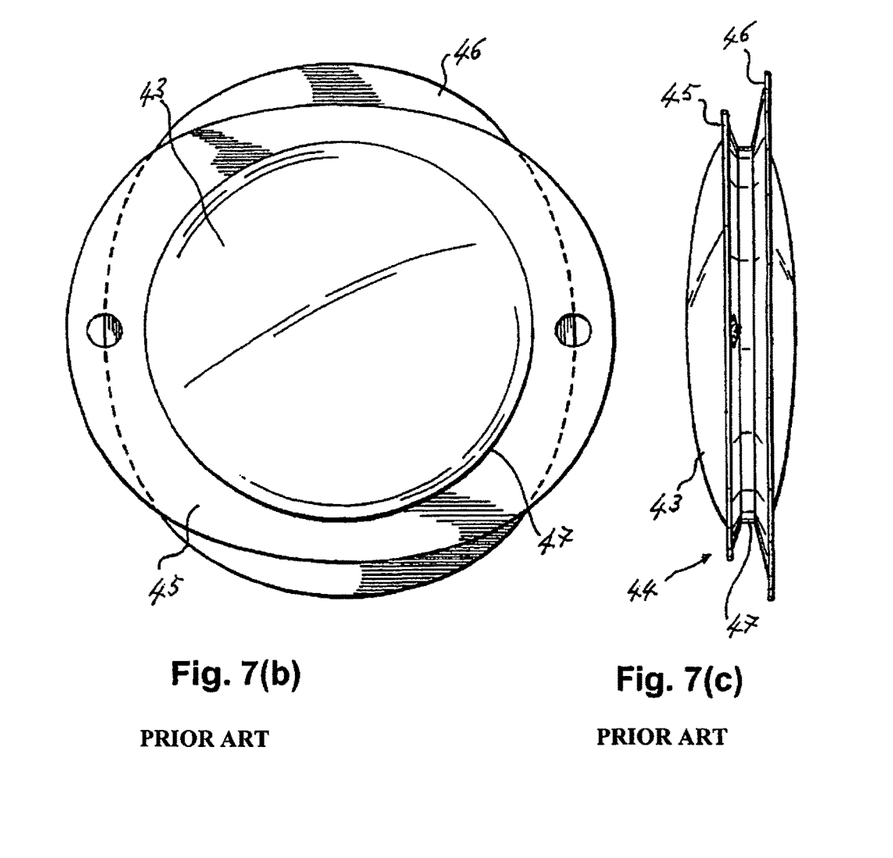

U.S. Pat. No. 6,027,531 describes a so-called "bag-in-lens" technique, in which the optical implant takes the form shown in FIGS. 7(a)-7(c). This implant comprises a lens optic 43 and a haptic portion 44 comprising an anterior lip 45 and a posterior lip 46. The haptic portion 44 is configured to form a groove 47, into which will be fitted the lips of a pair of capsulotomies formed respectively in the anterior and posterior walls of the capsule.

SUMMARY OF THE INVENTION

Figure 8:
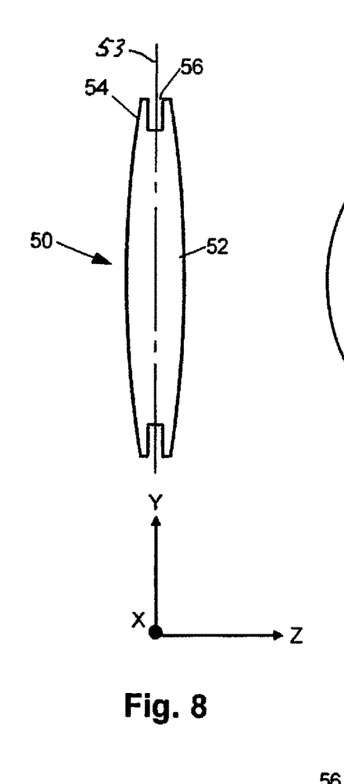
FIGS. 8 and 9 are side and front views, respectively, of an embodiment of an intraocular insert according to the present invention.
Figure 9:
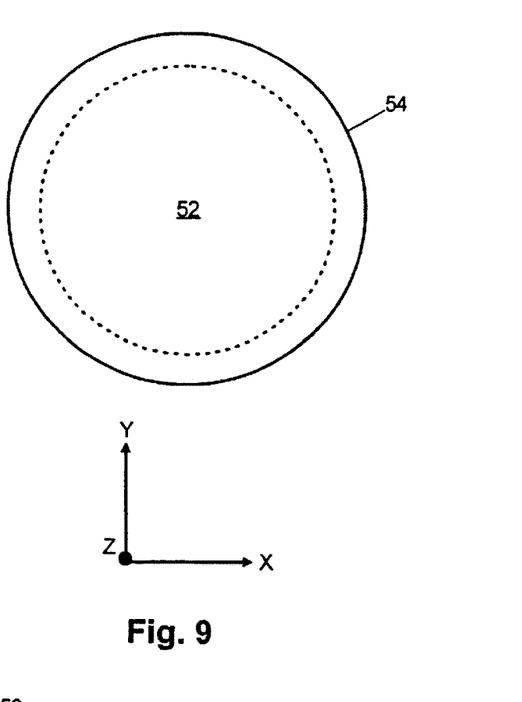

One problem associated with these known capsular insert techniques is that it is difficult to centre the lens accurately in the X-Y plane of the eye. The X-Y-Z co-ordinates are shown in FIGS. 8 and 9, where the radius of the lens lies in the X-Y plane and the Z-direction is parallel to the optical axis of the eye. A second problem is that it can be difficult to properly define the position of the lens in the Z-direction. This can lead to difficulties in accurately defining the optical power required for the artificial lens. A third problem, which one embodiment of the present invention can solve, is that, some time after the cataract operation has been carried out, the posterior wall of the capsule (the "posterior capsule") can become clouded or opaque like the original lens, requiring a further surgical intervention.

The present invention provides an intraocular implant comprising a main portion, which is a lamina, and a peripheral portion disposed at the periphery of the main portion, the peripheral portion comprising a groove for engagement with the lip of a single capsulotomy only formed in the lens capsule of the eye, the groove lying substantially parallel to the plane of the lamina. The groove may extend continuously around the peripheral portion of the implant.

Alternatively, it may be provided at discrete locations around the peripheral portion of the implant, in which case the discrete locations are, for example, substantially equidistant from each other.

The groove may be provided as a gap between a first projection from the main portion of the implant and a second projection from the main portion of the implant. Either the first projection and/or the second projection may be provided as a plate or as a loop, or the first projection is provided as a plate and the second projection is provided as a loop. The plate or loop is preferably rounded at its end.

The groove may include first and second grooves lying parallel to the plane of the lamina and spaced apart from each other in a direction orthogonal to said plane, the first groove being for engagement with the lip of an anterior capsulotomy and the second groove being for engagement with the lip of a posterior capsulotomy, the second groove being of smaller mean circumference than the first groove.

The implant may comprise a multi-lamina unit comprising first and second laminae spaced apart from each other in a direction orthogonal to the planes of the laminae, the first lamina having a first said groove and the second lamina having a second said groove, the first groove being for engagement with the lip of an anterior capsulotomy and the second groove being for engagement with the lip of a posterior capsulotomy, the second groove being of smaller mean circumference than the first groove.

The implant may further comprise at the peripheral portion thereof at least one lug for engagement with corresponding voids formed in the capsule. Two, three or four lugs may be provided spaced around the peripheral portion for engagement with respective voids formed in the capsule. The lugs are, for example, substantially equidistantly placed around the peripheral portion of the implant.

The implant may be a lens or a plug for occluding the capsulotomy. When it is a plug, the plug may be opaque and/or have zero optical power.

The invention also provides a method for fixing the intraocular implant into an eye, where the implant has a groove which extends continuously around the peripheral portion of the implant, the method comprising: forming a capsulotomy within the capsule of the eye, the capsulotomy having a profile matching that of the implant and having a circumference lying between the inner and outer circumferences of the groove of the implant; offering the implant up to the capsule, and inserting the lip of the capsulotomy into the groove, thereby securing the implant to the capsule.

The invention further provides a method for fixing the intraocular implant into an eye, where the implant has a groove at discrete locations around the peripheral portion of the implant, the method comprising: forming a capsulotomy within the capsule of the eye, the capsulotomy having a profile matching that of the implant and having a circumference lying between an inner circumference formed by the equidistantly spaced grooves and an outer circumference formed by the equidistantly spaced grooves; orienting the implant proximate to the capsule, and inserting the lip of the capsulotomy into the grooves, thereby securing the implant to the capsule.

Before the offering up step, there may be the step of surgically removing the natural crystalline lens material of the eye.

BRIEF DESCRIPTION OF THE DRAWINGS

Embodiments of the present invention will now be described, by way of example only, with the aid of the drawings, of which.

DETAILED DESCRIPTION

An embodiment of an intraocular implant in accordance with the present invention is illustrated in FIGS. 8 and 9, in which FIG. 8 is a side view and FIG. 9 is a front view of the implant.

Figure 10:
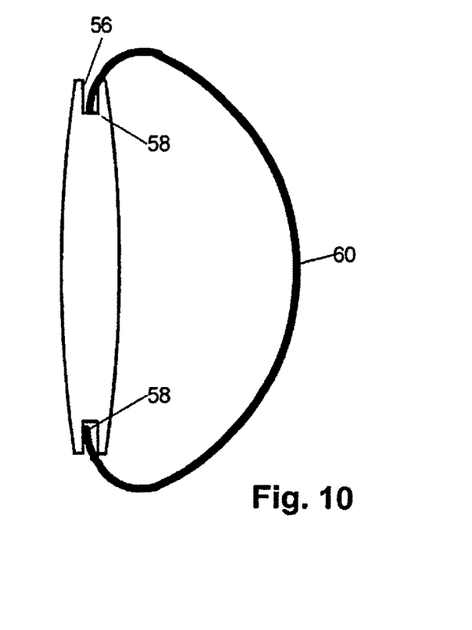
FIG. 10 is the side view according to FIG. 8 with the lens engaged with the capsule.

The implant in this embodiment is an artificial lens implant 50 for treating, e.g., cataracts, and comprises a lens body portion 52, which is the lens proper (the "optic"), and a peripheral portion 54. The peripheral portion 54 has formed in an axially approximately central part thereof (i.e. referred to the Z-axis) a groove 56, which extends in a radial direction from the periphery of the implant toward its optical axis. Thus, the groove 56 lies parallel to, and according to one embodiment in, the axially central plane 53 of a lamina constituted by the optic 52. The term "lamina" refers to a plate-like member having a surface area much greater than its thickness, especially at its outer edge. During the surgical procedure, the lens 50 is oriented proximate to the anterior capsulotomy, which has been formed by laser in the capsule 60 (see FIG. 10), as mentioned above in connection with the known implantation method, and the lip 58 of the capsulotomy is fitted into the groove 56, thereby holding the implant in place. Hence, this method dispenses with the need for haptics, instead relying on the lens itself for securing to the capsule. In addition, the correct positioning of the lens vis-à-vis the optical axis of the eye can be ensured by accurately locating the capsulotomy in the X-Y plane (see FIGS. 8 and 9). Thus, some eccentricity can be introduced into the radial positioning of the lens by this appropriate locating of the capsulotomy in the capsule.

It is desirable not only that the capsulotomy be accurately located in the capsule, but also that the size of the capsulotomy be accurately defined, so that it can fit the groove in the implant. This is possible at this present time, due to the existence of pulsed ultrafast femtosecond laser technology, by use of which extremely accurate cutting operations can be achieved in a reliable and repeatable manner.

Where desired, one or more fenestrations can be made in the capsule, in order to provide for the passage of a lens or device into the capsular bag or to allow the transfer of aqueous fluid.

Figure 11A:
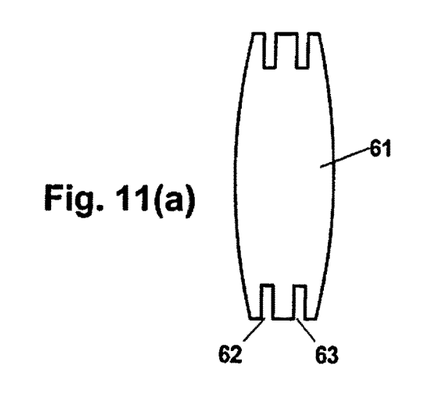
FIGS. 11(a) and 11(b) are a side view of a variant of an embodiment according to the invention.
Figure 11B:
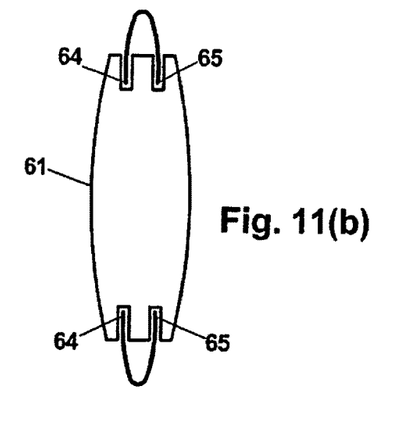

Although this embodiment has been described in connection with an anterior capsulotomy, in practice the implant may be made to engage with a posterior capsulotomy instead, or even with both types of capsulotomy at the same time. A realization of this latter arrangement is illustrated in FIGS. 11a and 11b, in which an implant comprises the optic portion 61 and a peripheral portion with a pair of annular grooves 62 and 63. These grooves are spaced apart from each other in the Z-direction (see FIG. 8) and are designed to take respective lips 64, 65 of an anterior and posterior capsulotomy (see FIG. 11b). A variant version of this arrangement is shown in the side and front views of FIGS. 12a and 12b, respectively. In this version the posterior capsulotomy is smaller than the anterior capsulotomy. To accommodate this, the anterior groove 66 has a larger mean periphery than the posterior groove 67. This is best explained with reference to FIG. 12b, in which the larger groove has an outer periphery 66' and an inner periphery 66", while the smaller groove has an outer periphery 67' and an inner periphery 67". The mean periphery of the groove 66 is clearly larger than that of the groove 67. For a circular profile, as illustrated, this means that the mean anterior diameter $D_A$ of the groove 66 is larger than the mean posterior diameter $D_P$ of the groove 67.

Figure 12A:
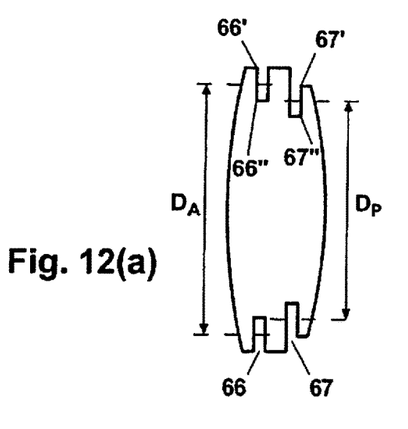
FIGS. 12(a), 12(b) and 12(c) are side and front views of a further variant of an embodiment according to the invention.
Figure 12B:
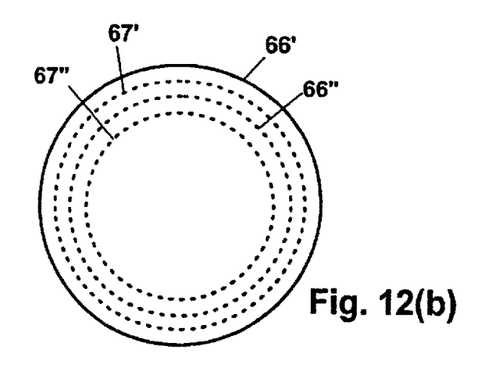
Figure 12C:
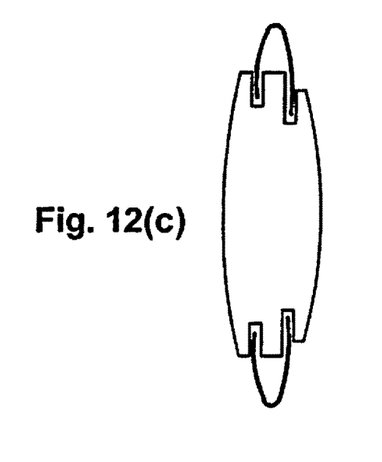

This version as fitted to the capsular bag is shown in FIG. 12c.

The FIG. 12 arrangement can be beneficial to a patient, since it is often desirable to limit the extent of the posterior capsulotomy, as this reduces risk of the lens implant being accidentally displaced through the posterior capsulotomy into the vitreous cavity.

Figure 13:
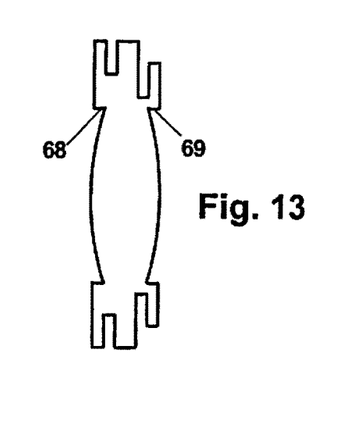
FIG. 13 is a side view of a yet further variant of an embodiment according to the invention.

One potential drawback of the arrangements illustrated in FIGS. 11 and 12 is that the provision of two grooves in the same lens can increase the thickness of the optic. To avoid this, the configuration of FIG. 13 may be employed. In this configuration the peripheral portion of the implant has either or both of an anterior overhang 68 and a posterior overhang 69, which allows a reduced thickness of the optic.

Figure 25:
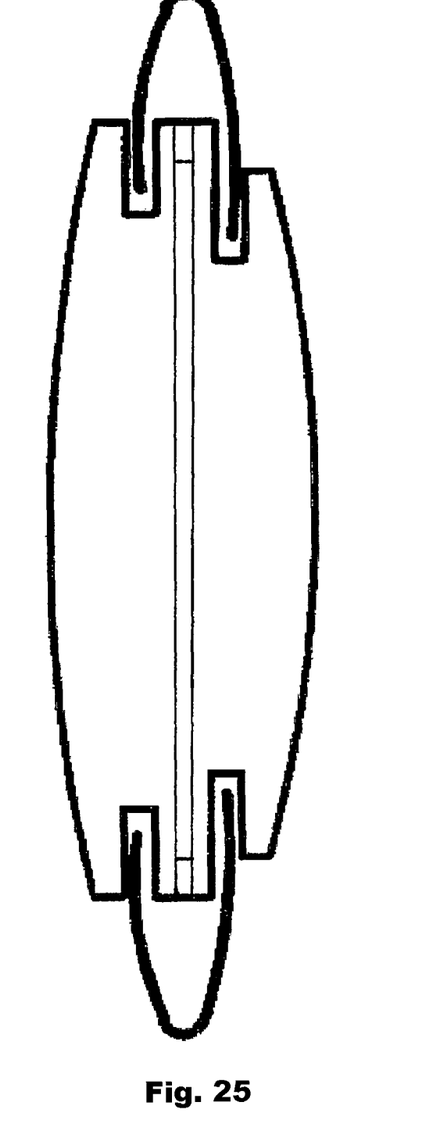
FIG. 25 is a side view of a further variant of an embodiment according to the invention

This embodiment also envisages the use of a complex-lens arrangement, for example depicted in FIG. 25, involving the use of more than one optic. In particular, two optics may be used, which are connected together to form a single unit. This apparatus may be fixated to the anterior capsulotomy or to a posterior capsulotomy, or to both. In the latter case, the two capsulotomies engage with two different spaced-apart grooves.

Figure 14:
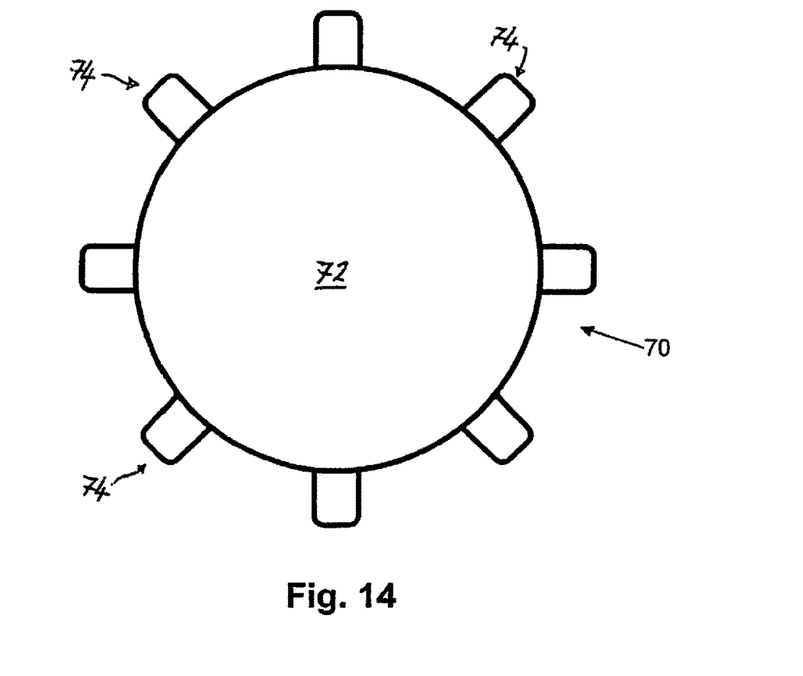
FIGS. 14 and 15 are front and plan views, respectively, of another embodiment of an intraocular insert according to the present invention.
Figure 15:
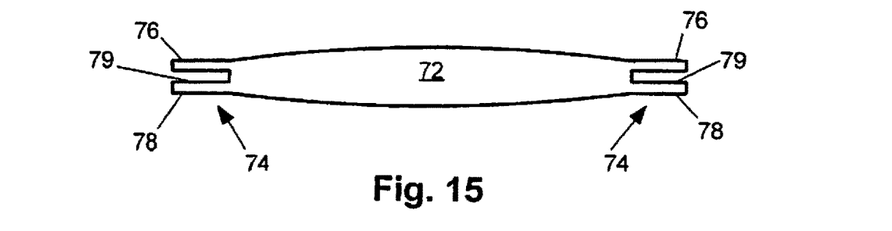
Figure 16:
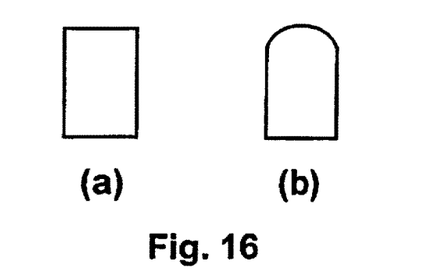
FIGS. 16(a) and 16(b) are different realizations of the projections shown in FIGS. 14 and 15.

Another embodiment of the invention is illustrated in FIGS. 14 and 15. Here a lens 70 has an optic portion 72 and a series of projection portions 74 projecting from the circumference of the lens portion. Referring to the plan view of FIG. 15, each projection portion comprises a first projection 76 and a second projection 78, which are disposed at opposite sides of the lens, and a gap 79 between the first and second projections. The gap 79 corresponds to the groove 54 in FIG. 8. The projections 76 and 78 may be rectangular or rounded in shape, or a combination of both (see FIGS. 16(a) and 16(b)). Hence the projections 76 may be rectangular, while the projections 78 are rounded, or vice-versa, or any combination of the two around the periphery of the implant, or the projections may be all of one type. In practice, the rounded configuration is preferred for all of the projections, since this makes it easier to fit the capsulotomy to the implant and also reduces the risk of trauma to the capsule that a sharp edge of the rectangular profile might cause. The projections are either integral to the optic (i.e. molded), or they may be attached to the body of the lens by some suitable means (e.g. mechanical slot and groove) and can be of the same material as the lens optic or of a different biocompatible material. The projections are either in the form of thin loops or plates. Although eight projection pairs have been shown, the invention is not limited to this number. More or less than eight may be used. A criterion for selecting the appropriate number is the reliability and stability of the attachment of the lens to the capsule.

Figure 17:
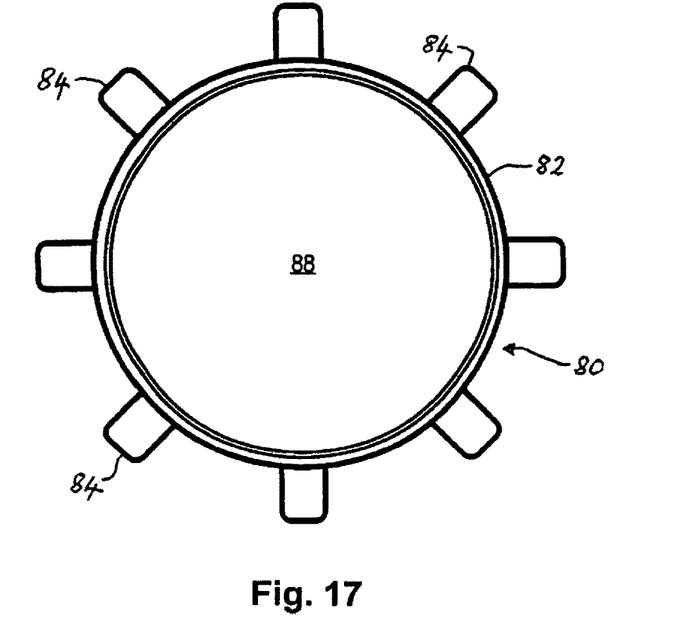
FIGS. 17 and 18 are front and plan views, respectively, of a variant of an embodiment.
Figure 18:
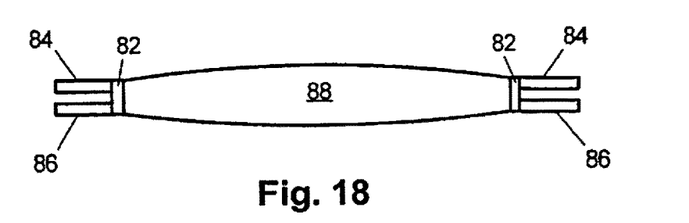

In a variant of the embodiment just described, the projections are not integral with the optic, or attached directly to the optic, but instead form part of a separate projection unit, which is fitted to the optic. This is shown in FIGS. 17 and 18, in which the projection unit 80 comprises an annular frame 82, which is tightly fitted to the optic 88, and attached to which are pairs of projections 84, 86.

Figure 19:
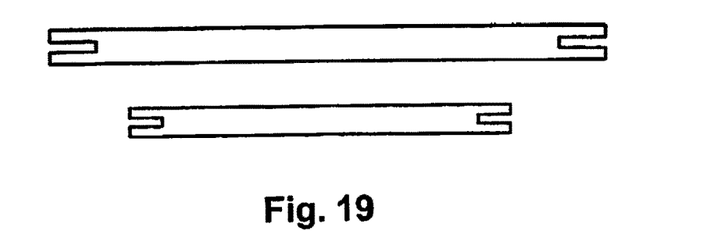
FIG. 19 shows two different examples of another embodiment of an intraocular implant according to the present invention.

In another embodiment of the present invention, the intraocular implant of the first embodiment is not a lens, but a plug or bung. Such an implant is not required to have any optical power, but serves merely to close a fenestration or other aperture in the capsule. An example of this is shown in FIG. 19. Indeed, FIG. 19 shows two examples of different diameter, depending on the size of the fenestration to be closed. It can be seen that this implant is flat and therefore has no optical power. Depending on the position of the fenestration being closed, the plug may also be opaque, partially opaque, translucent or otherwise optically altered from transparent.

Fenestrations that might be closed off using the plug are, for example, fenestrations introduced into the capsule in order to facilitate the entry of an instrument for evacuating the lens material. In this respect, femtosecond lasers are often used to cut the lens into very small cubes or slices, so that they can be evacuated through a small-bore instrument or cannula. The cannula can be introduced into the capsule through such a fenestration. In addition, the plug can be used to provide tectonic support, in order to keep compartments in the eye physically separate. Such an embodiment can be used to provide a barrier between the vitreous chamber and the anterior chamber after capsulotomy for example to inhibit vitreous prolapsed. It is also useful as a means of preventing silicone oil from moving forward into the anterior segment of the eye from the vitreous chamber.

Still another embodiment will now be described.

This embodiment recognizes that there is often a need to rotationally align a lens implant, where there is an asymmetrical optic (e.g. where there is variable optical power in the lens or where there is a toric optic). This embodiment utilizes forward or backward facing lugs, which are placed in voids (e.g. fenestrations or very small capsulotomy holes) created in the capsule. These voids are located radially outside the main capsulotomy and can be formed by photoablation via a laser.

Figure 20:
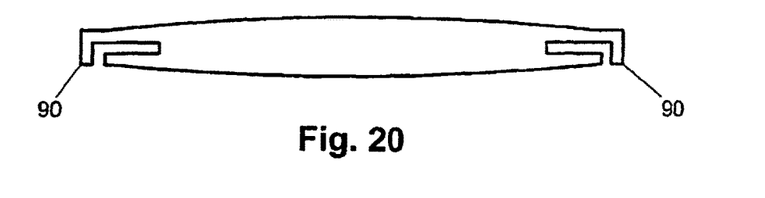
FIG. 20 is a plan view of an intraocular implant illustrating the principle of another embodiment of the present invention.

The principle of this embodiment is illustrated in FIG. 20. In FIG. 20 a lens implant such as shown in FIG. 8 or FIG. 15 is provided with one or more lugs 90 situated radially outwardly of the outer ends of the groove 56 or projections 76, 78.

Figure 21:
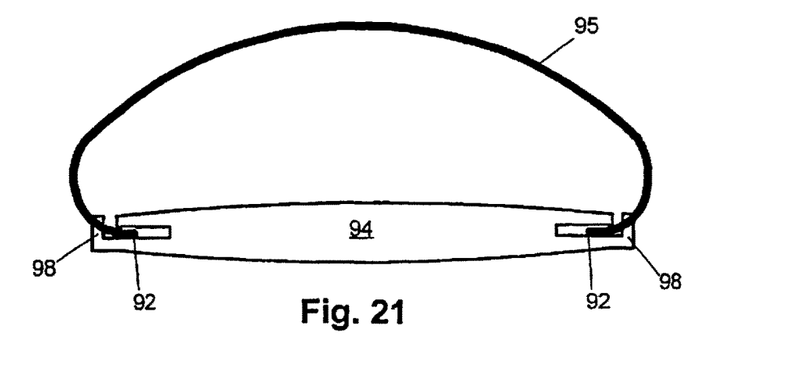
FIGS. 21 and 22 are plan and front views, respectively, of one realization of the embodiment of FIG. 20, FIGS. 23 and 24 are plan and front views, respectively, of another realization of the embodiment of FIG. 20.
Figure 22:
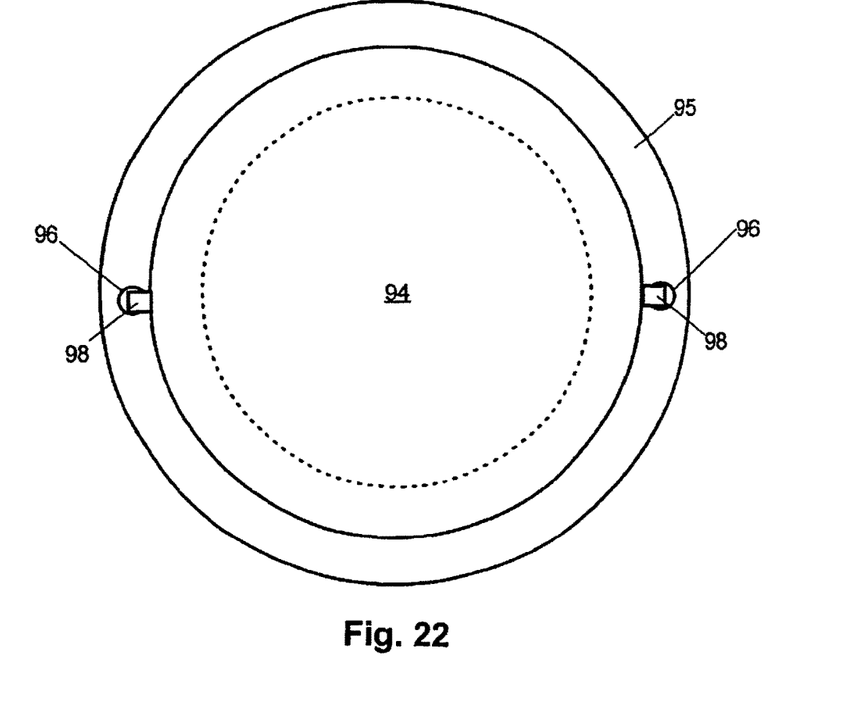

FIGS. 21 and 22 illustrate one specific realization or example of this embodiment, based on the first embodiment. As in FIG. 10, the lip 92 of the capsulotomy in this embodiment is engaged in the groove of the lens 94. Holes 96 have been formed in the capsule 95 and a pair of oppositely disposed lugs 98, which are integral with the lens, are made to engage with these holes, thereby securing the lens in a given rotational position relative to the capsule. In this arrangement the implant is oriented so that the lugs face toward the back of the eye. Instead, the lens may be reversed, so that the lugs face toward the front of the eye and therefore engage with the residual anterior capsule from an inside surface thereof instead of from the outside surface thereof, as in FIG. 21.

Figure 23:
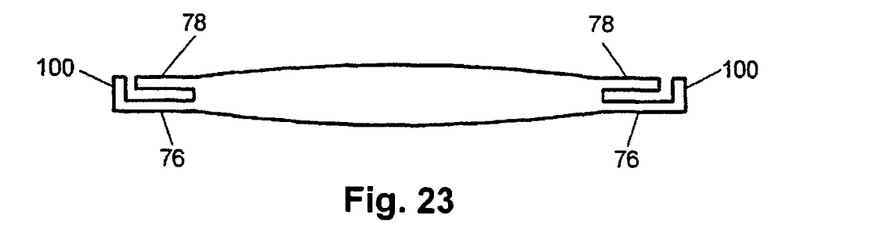
Figure 24:
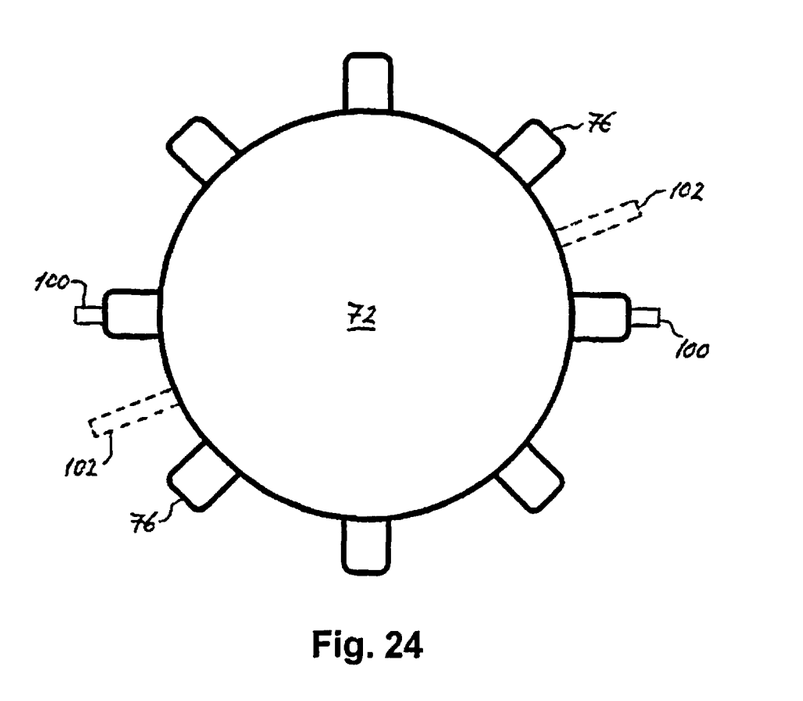

A variant of this arrangement is shown in FIGS. 23 and 24, and is based on the second embodiment. Here a pair of oppositely placed lugs 100 is provided as integral extensions to two of the first projections 76 or second projections 78. These engage with holes or voids in the capsule similar to those shown in FIG. 22. In a further variant of this variant arrangement, the lugs are instead each provided between two adjacent projections 76 or 78, as shown by the dotted-line projections 102 in FIG. 24. These projections 102 are therefore dedicated solely to carrying the lugs, whereas in the first arrangement the projections 76 (or 78) act both as protrusions for engagement with the lip of the capsulotomy and as carriers of the lugs for engagement with the capsule.

Although the lugs shown in FIGS. 20, 21 and 23 are of a length such as to end up approximately flush with the radially outer part of the projecting portion—e.g. flush with the projections 78 in FIG. 23, and similarly in FIG. 21—in practice the lugs will have a length such as to enable them to be readily fitted into the voids in the capsule wall, with at the same time the capsule lip being fitted into the groove(s). As shown in FIG. 21, the lugs preferably pass right through through-holes made in the capsule wall, and will therefore be of a length, which enables them to do that, while not being so long that they make it difficult to fit the capsule lip into the groove(s).

As regards the end-profile of the lugs (that is, looking down onto the end of the lugs), this is preferably circular, though other profiles may also be suitable, provided they are able to engage with the voids made in the capsule.

Instead of two lugs per lens, only one may be employed, or more than two—e.g. three or four. They will generally be equally distributed around the periphery of the lens.

Some advantages of the present invention are as follows:
- accurate positioning of the lens in the X-Y plane over the pupil centre or any desired centre-point (e.g. the line of sight);
- potentially more accurate placement in the Z-direction, due to the sitting of the lens in the anterior or posterior part of the capsule;
- if the lens is supported by the posterior part of the capsule, then the opacification or clouding, to which the posterior capsule is often subject post-op, cannot occur;
- the insert can take the form of a plug or blank instead of a lens, which can be used to seal or obstruct a capsular opening used during surgery;
- such a plug may comprise a valve arrangement to allow the passage of fluid, which can regulate the volume of the capsule;
- because there is predictable positioning of the lens in the Z-direction, then a more reliable biometry formula can be written for example for lens power calculation;
- since the insert is secured by the rim of the capsulotomy, its rotational position can be defined by the forming of marker voids or fenestrations in the capsule and of lugs as extensions to the lens, which engage with the fenestrations;
- the provision of two grooves axially spaced apart in the implant allows anterior and posterior capsulotomies of different sizes to be engaged with the implant, since each capsulotomy is allocated to its own groove.

Although the implant has been described for use with the human eye, it can equally well be used with the animal eye.

In addition, although implants of circular profile have been shown in connection with the various embodiments, the profile used can be any desired profile thought to be appropriate to the situation in question. Thus, oval or elliptical profiles are possible, for instance.

As regards the materials used for the implant any of the materials used for intraocular lens implants, such as acrylic, silicone or hydrogel materials, are suitable.

The implant of the present invention has been described in connection with its use in cataract operations. However, it may also be used for treating myopia, hyperopia, astigmatism or presbyopia (refractive lens exchange surgery).

The implant may also be used in piggyback situations where the natural lens is left in place and the implant lens is also placed in the eye.

The foregoing description has been given by way of example only and it will be appreciated by a person skilled in the art that modifications can be made without departing from the scope of the present invention.

The invention claimed is:

1. An intraocular lens implant for placement in the eye, the implant comprising:
   a main portion, which is a lamina, the lamina extending along a plane, and a peripheral portion disposed at a periphery of the main portion, the peripheral portion comprising a first groove, the first groove being defined by a first gap between a first projection and a second projection of the peripheral portion, the first projection and the second projection extending radially outward from the main portion and the first groove being structured and sized to engage a first lip of a first capsulotomy formed in the anterior lens capsule of the eye such that the first lip of the anterior lens capsule of the eye is received in the first groove between the first projection and the second projection;
   the peripheral portion further comprising a third projection extending radially outward from the main portion and defining together with the second projection a second groove lying parallel to the plane of the lamina and spaced apart from the first groove in a direction orthogonal to said plane, the second groove being structured and sized to engage a second lip of a second capsulotomy formed in a posterior lens capsule of the eye between the second projection and the third projection, each of the anterior and posterior lens capsule being respectively, separately receivable in the first groove and the second groove.

2. The intraocular implant as claimed in claim 1, wherein the groove extends continuously around the peripheral portion of the implant.

3. The intraocular implant as claimed in claim 1, wherein either the first projection and/or the second projection comprises a plate.

4. The intraocular implant as claimed in claim 3, wherein the plate is rounded at an end thereof.

5. The intraocular implant as claimed in claim 1, wherein either the first projection and/or the second projection is comprises a loop.

6. The intraocular implant as claimed in claim 5, wherein the loop is rounded at an end thereof.

7. The intraocular implant as claimed in claim 5, wherein the first projection comprises a plate and the second projection comprises a loop.

8. The intraocular implant as claimed in claim 7, wherein the plate or loop is rounded at an end thereof.

9. The intraocular implant as claimed in claim 1, wherein the main portion comprises a multi-lamina unit comprising first and second laminae spaced apart from each other in a direction orthogonal to the planes of the laminae, the first lamina having the first groove and the second lamina having the second groove, the first groove being for engagement with the lip of an anterior capsulotomy and the second groove being for engagement with the lip of a posterior capsulotomy, the second groove being of smaller mean circumference than the first groove.

10. The intraocular implant as claimed in claim 1, wherein the implant further comprises at the peripheral portion thereof at least one lug for engagement with corresponding voids formed in the capsule.

11. The intraocular implant as claimed in claim 10, comprising two, three or four lugs spaced around the peripheral portion configured for engagement with respective voids formed in the capsule.

12. The intraocular implant as claimed in claim 11, wherein the lugs are substantially equidistantly placed around the peripheral portion of the implant.

13. The intraocular implant as claimed in claim 1, wherein the main portion comprises a lens having refractive power.

14. The intraocular implant as claimed in claim 1, wherein the implant comprises currently Amended a plug for occluding the capsulotomy.

15. The intraocular implant as claimed in claim 14, wherein the plug is opaque.

16. The intraocular implant as claimed in claim 14, wherein the plug has zero refractive power.

\* \* \* \* \*